(12) United States Patent
Riistama et al.

(10) Patent No.: US 10,531,842 B2
(45) Date of Patent: Jan. 14, 2020

(54) METHOD AND APPARATUS FOR ADJUSTING A MONITORING SYSTEM

(71) Applicant: KONINKLIJKE PHILIPS N.V., Eindhoven (NL)

(72) Inventors: Jarno Mikael Riistama, Waalre (NL); Gerhard Spekowius, Staelen (DE); Joseph Ernest Rock, Littleton, MA (US); Emile Josephus Carlos Kelkboom, Eindhoven (NL); Silviu Dovancescu, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 94 days.

(21) Appl. No.: 15/534,871

(22) PCT Filed: Dec. 9, 2015

(86) PCT No.: PCT/EP2015/079143
§ 371 (c)(1),
(2) Date: Jun. 9, 2017

(87) PCT Pub. No.: WO2016/091961
PCT Pub. Date: Jun. 16, 2016

(65) Prior Publication Data
US 2018/0263573 A1 Sep. 20, 2018

Related U.S. Application Data (60) Provisional application No. 62/090,161, filed on Dec. 10, 2014.

(30) Foreign Application Priority Data

Jan. 26, 2015 (EP) .................................... 15152481

(51) Int. Cl.
*A61B 5/00* (2006.01)
*A61B 5/0205* (2006.01)
(Continued)

(52) U.S. Cl.
CPC ............ *A61B 5/746* (2013.01); *A61B 5/0205* (2013.01); *A61B 5/02438* (2013.01); *A61B 5/0531* (2013.01); *A61B 5/6805* (2013.01)

(58) Field of Classification Search
CPC ...... G06F 19/00; G06F 19/3418; G16H 50/20
(Continued)

(56) References Cited

U.S. PATENT DOCUMENTS

| 5,876,353 A * | 3/1999 | Riff ...................... A61B 5/0535 600/529 |
| 5,957,861 A * | 9/1999 | Combs ................. A61B 5/0535 600/481 |

(Continued)

FOREIGN PATENT DOCUMENTS

WO 2014091426 A1 6/2014

*Primary Examiner* — Carl H Layno
*Assistant Examiner* — Michael J Lau (57) ABSTRACT

There is provided a method and apparatus for adjusting a monitoring system which is arranged to receive measured values of a physiological characteristic of a subject and to generate an alarm when the received measured values meet at least one predefined alarm generation criterion. The method comprises obtaining data relating to a hospitalization of the subject, the data comprising a time of the hospitalization; obtaining a plurality of measured values of the physiological characteristic measured during a measurement period preceding the time of the hospitalization or a measurement period preceding and including the time of the hospitalization; defining a detection window as a time period ending with the time of the hospitalization and having a predetermined duration; determining whether the monitoring system would generate an alarm during the detection (Continued)

window based on applying the at least one predefined alarm generation criterion to the obtained plurality of measured values; and if the monitoring system would not generate an alarm during the detection window, altering the at least one predefined alarm generation criterion such that the time at which the monitoring system would generate an alarm based on applying the altered predefined alarm generation criterion to the obtained plurality of measured values is within the detection window.

15 Claims, 6 Drawing Sheets (51) Int. Cl.
  *A61B 5/024* (2006.01)
  *A61B 5/053* (2006.01)
(58) Field of Classification Search
  USPC .......................................................... 600/301
  See application file for complete search history.

(56) References Cited

U.S. PATENT DOCUMENTS

| | | | | |
|---|---|---|---|---|
| 6,038,469 | A * | 3/2000 | Karlsson | A61B 5/0006 600/509 |
| 6,512,949 | B1 * | 1/2003 | Combs | A61B 5/0535 600/547 |
| 6,876,972 | B1 * | 4/2005 | Kameda | G06Q 50/24 705/3 |
| 2002/0103676 | A1 * | 8/2002 | Yamaguchi | G06Q 50/24 705/3 |
| 2003/0214409 | A1 | 11/2003 | Hickle | |
| 2006/0030890 | A1 * | 2/2006 | Cosentino | A61B 5/00 607/5 |
| 2007/0016451 | A1 * | 1/2007 | Tilson | A61B 5/00 705/3 |
| 2007/0093721 | A1 * | 4/2007 | Lynn | A61B 5/14551 600/532 |
| 2007/0273504 | A1 * | 11/2007 | Tran | A61B 5/0022 340/539.12 |
| 2008/0126132 | A1 * | 5/2008 | Warner | A61B 5/0002 705/3 |
| 2008/0306764 | A1 * | 12/2008 | Weiss-Meilik | G06Q 50/22 705/2 |
| 2009/0192824 | A1 * | 7/2009 | Minakuchi | G06F 19/321 705/3 |
| 2010/0022911 | A1 * | 1/2010 | Wariar | A61B 5/021 600/561 |
| 2011/0009760 | A1 * | 1/2011 | Zhang | A61B 5/08 600/529 |
| 2011/0106201 | A1 * | 5/2011 | Bhunia | A61B 5/1459 607/18 |
| 2011/0106213 | A1 * | 5/2011 | Davis | G16H 40/63 607/59 |
| 2011/0190580 | A1 * | 8/2011 | Bennett | A61B 1/00016 600/109 |
| 2011/0190647 | A1 * | 8/2011 | Helfenbein | A61B 5/0452 600/509 |
| 2012/0046965 | A1 * | 2/2012 | Ryan | G06Q 10/10 705/2 |
| 2012/0116194 | A1 * | 5/2012 | Gross | A61B 5/00 600/324 |
| 2012/0253207 | A1 * | 10/2012 | Sarkar | A61B 5/0004 600/483 |
| 2013/0012830 | A1 * | 1/2013 | Leininger | A61B 5/0488 600/546 |
| 2013/0291060 | A1 * | 10/2013 | Moore | G06F 21/6245 726/1 |
| 2014/0266786 | A1 * | 9/2014 | Sugiyama | A61B 5/742 340/870.4 |
| 2014/0276164 | A1 * | 9/2014 | Thakur | A61B 5/686 600/528 |
| 2014/0278463 | A1 * | 9/2014 | Merry | G16H 40/63 705/2 |
| 2014/0324459 | A1 * | 10/2014 | Barfield | G06F 19/3418 705/3 |

* cited by examiner

METHOD AND APPARATUS FOR ADJUSTING A MONITORING SYSTEM

This application is the U.S. National Phase application under 35 U.S.C. § 371 of International Application No. PCT/EP2015/079143, filed on Dec. 9, 2015, which claims the benefit of European Application Serial No. 15152481.6, filed Jan. 26, 2015 and of U.S. Provisional Application Ser. No. 62/090,161, filed Dec. 10, 2014. These applications are hereby incorporated by reference herein.

TECHNICAL FIELD OF THE INVENTION

The invention relates to a method and apparatus for adjusting a monitoring system, and in particular to a method and apparatus for adjusting a monitoring system for use in monitoring a health condition of a subject.

BACKGROUND TO THE INVENTION

Pulmonary congestion is a clinical condition that is caused by a number of different diseases such as heart failure or kidney disease. It consists of an accumulation of fluid in the interstitial and alveolar space of the lung following increased blood pressure in the pulmonary capillary vessels that leads to leakage of water from the blood to the lung space. It causes fluid retention and fluid redistribution in the body and leads to symptoms like dyspnea, fatigue, and activity intolerance. Pulmonary congestion resulting from elevated left atrial and left ventricular filling pressures is a main reason for heart failure hospitalization. This condition has a progressive nature and clinical signs and symptoms of pulmonary oedema occur late, typically when the lung fluid has increased at least six-fold from the initial stage of interstitial oedema. This means that pulmonary oedema is often not detected early, and necessary treatment for the patient is delayed.

Bio-impedance measurements, obtained by a bio-impedance monitor using, for example, external electrodes or an implanted device to measure the resistance of biological tissue to a small alternating current flowing across a region of interest, e.g. the thorax, can be used to detect pulmonary congestion. The principle underlying this technique is the fact that the electrical impedance (resistance and reactance) of biological tissue is directly linked to the hydration and water content of the tissue, namely intra-cellular and extra-cellular water. When thoracic fluid accumulates (e.g. during pulmonary congestion), there will be a better conductance of the current resulting in a decreased impedance. By measuring the impedance at different frequencies the resistance of the extracellular water ($R_e$) can be estimated according to the Cole-Cole model. Therefore, measurements of the electrical properties of the tissue can indicate the amount of fluid present in that part of the body.

If external electrodes are used, impedance measurements are influenced by several factors including sensor placement, skin moisture, body dimensions and body posture. It has been found that body dimensions and fat mass are particularly relevant to thoracic impedance measurements, making such measurements subject-specific. Implantable devices are not affected by variations in electrode placement or skin moisture; however, it is known that the measurements made by such devices have variability due to less controlled measurement conditions (the patient may be unaware that a measurement is being taken and so measurements may be obtained in a variety of situations which would cause differing fluid distribution in the body, such as lying down, sitting, walking, or exercising). These factors, combined with the normal variability of bio-impedance measurements, make it challenging to determine when an impedance measurement for a specific patient is abnormal and thus indicative of excess fluid accumulation. Furthermore, studies have shown that the deterioration of heart failure patients and related changes in bio-impedance can occur over a different timespan for each patient. When bio-impedance is monitored, this can mean that false alarms are often generated for patients who deteriorate slowly, and/or that alarms are not generated soon enough for patients who deteriorate quickly.

WO 2014/091426 describes an algorithm for detecting abnormal measurements which defines and continuously updates a subject-specific range of normal variability for bio-impedance, using the measurements obtained from a subject. However; this algorithm does not provide a way to account for the variability between patients of the deterioration timespan.

A more reliable means of fluid content monitoring would be a valuable tool to improve outcomes in heart failure hospitalizations and reduce healthcare costs. There is therefore a need for an improved method and apparatus that can more reliably determine whether a given sequence of abnormal bio-impedance values obtained from a given subject are indicative of deterioration in that subject's heart failure condition, and that can raise an alarm at an appropriate time for any given subject. Such a method and apparatus could be used in a home or hospital-based monitoring system to detect the presence and progression of pulmonary congestion, as well as for monitoring improvements in the patient's condition as a result of receiving treatment. Such a method and apparatus could also be used in monitoring other physiological characteristics of a subject, such as weight, heart rate, blood pressure, temperature, etc., where low or alternatively high values of the physiological characteristic indicates that the subject has (or the degree to which the subject has) a physiological condition.

SUMMARY OF THE INVENTION

According to a first aspect of the invention, there is provided a method for adjusting a monitoring system, wherein the monitoring system is arranged to receive measured values of a physiological characteristic of a subject and to generate an alarm when the received measured values meet at least one predefined alarm generation criterion; the method comprising:

obtaining data relating to a hospitalization of the subject, the data comprising a time of the hospitalization;

obtaining a plurality of measured values of the physiological characteristic measured during a measurement period preceding the time of the hospitalization or a measurement period preceding and including the time of the hospitalization;

defining a detection window as a time period ending with the time of the hospitalization and having a predetermined duration;

determining whether the monitoring system would generate an alarm during the detection window based on applying the at least one predefined alarm generation criterion to the obtained plurality of measured values; and if the monitoring system would not generate an alarm during the detection window, altering the at least one predefined alarm generation criterion such that the time at which the monitoring system would generate an alarm based on applying the altered predefined alarm generation criterion to the obtained plurality of measured values is different to the time at which the monitoring system would generate an alarm based on applying the unaltered predefined alarm generation criterion to the obtained plurality of measured values.

In a second aspect, there is provided a method for adjusting a monitoring system, wherein the monitoring system is arranged to receive measured values of a physiological characteristic of a subject and to generate an alarm when the received measured values meet at least one predefined alarm generation criterion; the method comprising:

obtaining data relating to a hospitalization of the subject, the data comprising a time of the hospitalization;

obtaining a plurality of measured values of the physiological characteristic measured during a measurement period preceding the time of the hospitalization or a measurement period preceding and including the time of the hospitalization;

defining a detection window as a time period ending with the time of the hospitalization and having a predetermined duration;

determining whether the monitoring system would generate an alarm during the detection window based on applying the at least one predefined alarm generation criterion to the obtained plurality of measured values; and if the monitoring system would not generate an alarm during the detection window, altering the at least one predefined alarm generation criterion such that the time at which the monitoring system would generate an alarm based on applying the altered predefined alarm generation criterion to the obtained plurality of measured values is within the detection window.

Thus, embodiments of the invention provide a monitoring system which can be personalized to the deterioration timespan of any given patient. Consequently, the system can more reliably determine when a sequence of abnormal values is indicative of a deterioration, and can generate an alarm at an optimal time (i.e. late enough that there is relatively high certainty that a deterioration is occurring, and early enough that treatment to prevent a hospitalization can be administered). Advantageously, this means that the false-positive rate and false-negative rate of monitoring systems can be significantly lowered (in other words both the sensitivity and the specificity can be improved) by applying embodiments of the invention to such systems.

The following embodiments relate to the above first and second aspects.

In some embodiments the method further comprises a step of determining whether the monitoring system would generate an alarm before the time of the hospitalization based on applying the at least one predefined alarm generation criterion to the obtained plurality of measured values. In such embodiments, if it is determined that the monitoring system would not generate an alarm before the time of the hospitalization, altering the at least one predefined alarm generation criterion comprises adjusting the sensitivity of the monitoring system; and if it is determined that the monitoring system would generate an alarm before the time of the hospitalization, and it is determined that the monitoring system would not generate an alarm during the detection window, altering the at least one predefined alarm generation criterion comprises adjusting the specificity of the monitoring system.

In some embodiments the at least one predefined alarm generation criterion comprises a time-based condition, and wherein altering the at least one predefined alarm generation criterion comprises altering the time-based condition. In some such embodiments the time-based condition is defined such that a predefined minimum number, N, of consecutive received measured values of the physiological characteristic must meet a predefined abnormality condition in order for the monitoring system to generate an alarm. In such embodiments altering the time-based condition comprises changing the value of N.

In some embodiments in which altering the at least one predefined alarm generation criterion comprises adjusting the sensitivity of the monitoring system, adjusting the sensitivity of the monitoring system comprises:

(i) setting the value of N to a first value, wherein the first value is equal to the greater of: one less than a current value of N and two;

(ii) operating the monitoring system on the basis of the obtained plurality of measured values and the first value of N;

(iii) determining whether operating the monitoring system generated an alarm within the detection window; and (iv) if operating the monitoring system did not generate an alarm within the detection window and the current value of N is greater than two, repeating steps (i)-(iii); or, if operating the monitoring system did not generate an alarm within the detection window and the current value of N is less than or equal to two, setting the value of N to equal two.

In some embodiments in which altering the at least one predefined alarm generation criterion comprises adjusting the specificity of the monitoring system, adjusting the specificity of the monitoring system comprises:

(a) setting the value of N to a second value, wherein the second value is one greater than the current value of N;

(b) operating the monitoring system on the basis of the obtained plurality of measured values and the second value of N;

(c) determining whether operating the monitoring system generated an alarm within the detection window; and (d) if operating the monitoring system did not generated an alarm within the detection window, repeating steps (a)-(c).

In some embodiments the obtained plurality of measured values comprises measured values received by the monitoring system. In such embodiments obtaining the plurality of measured values comprises accessing a memory used by the monitoring system to store received measured values. In some alternative embodiments the obtained plurality of measured values comprises measured values which have not been received by the monitoring system. In such alternative embodiments obtaining the plurality of measured values comprises obtaining measured values from a source not associated with the monitoring system.

In some embodiments the method further comprises determining whether the obtained plurality of measured values meets at least one predefined quality criterion; and, if the obtained plurality of measured values does not meet the predefined quality criterion; maintaining the current value of the at least one predefined alarm generation criterion.

In some embodiments the measurement period begins at least 2 days before the time of the hospitalization.

In some embodiments the method further comprises, if the monitoring system would generate an alarm during the detection window based on applying the at least one predefined criterion to the obtained plurality of measured values, adding an entry to a log of alarms without sufficient action.

In some embodiments the data relating to a hospitalization of the subject comprises information indicating a cause of the hospitalization. In such embodiments the method further comprises determining whether the cause of the hospitalization is related to a health condition being monitored by the monitoring system; and, if the cause of the hospitalization is not related to a health condition being monitored by the system, maintaining the current value of the at least one predefined alarm generation criterion.

In some embodiments the monitoring system is arranged to monitor heart failure. In some such embodiments the physiological characteristic is bio-impedance.

There is also provided, according to a third aspect of the invention, a computer program product, comprising computer readable code embodied therein, the computer readable code being configured such that, on execution by a suitable computer or processor, the computer or processor performs the method of the first or second aspect.

There is also provided, according to a fourth aspect of the invention, an apparatus for adjusting a monitoring system, wherein the monitoring system is arranged to receive measured values of a physiological characteristic of a subject and to generate an alarm when the received measured values meet at least one predefined alarm generation criterion. The apparatus comprises a processing unit arranged to:

obtain data relating to a hospitalization of the subject, the data comprising a time of the hospitalization;

obtain a plurality of measured values of the physiological characteristic measured during a measurement period preceding the time of the hospitalization or a measurement period preceding and including the time of the hospitalization;

define a detection window as a time period ending with the time of the hospitalization and having a predetermined duration;

determine whether the monitoring system would generate an alarm during the detection window based on applying the at least one predefined alarm generation criterion to the obtained plurality of measured values; and if the monitoring system would not generate an alarm during the detection window, alter the at least one predefined alarm generation criterion such that the time at which the monitoring system would generate an alarm based on applying the altered predefined alarm generation criterion to the obtained plurality of measured values is different to the time at which the monitoring system would generate an alarm based on applying the unaltered predefined alarm generation criterion to the obtained plurality of measured values.

According to a fifth aspect of the invention, there is provided an apparatus for adjusting a monitoring system, wherein the monitoring system is arranged to receive measured values of a physiological characteristic of a subject and to generate an alarm when the received measured values meet at least one predefined alarm generation criterion. The apparatus comprises a processing unit arranged to:

obtain data relating to a hospitalization of the subject, the data comprising a time of the hospitalization;

obtain a plurality of measured values of the physiological characteristic measured during a measurement period preceding the time of the hospitalization or a measurement period preceding and including the time of the hospitalization;

define a detection window as a time period ending with the time of the hospitalization and having a predetermined duration;

determine whether the monitoring system would generate an alarm during the detection window based on applying the at least one predefined alarm generation criterion to the obtained plurality of measured values; and if the monitoring system would not generate an alarm during the detection window, alter the at least one predefined alarm generation criterion such that the time at which the monitoring system would generate an alarm based on applying the altered predefined alarm generation criterion to the obtained plurality of measured values is within the detection window.

The following embodiments relate to the above fourth and fifth aspects.

In some embodiments, the processing unit is further arranged to determine whether the monitoring system would generate an alarm before the time of the hospitalization based on applying the at least one predefined alarm generation criterion to the obtained plurality of measured values. In some such embodiments, if it is determined that the monitoring system would not generate an alarm before the time of the hospitalization, the processing unit is arranged to alter the at least one predefined alarm generation criterion by adjusting the sensitivity of the monitoring system. In some such embodiments, if it is determined that the monitoring system would generate an alarm before the time of the hospitalization, and it is determined that the monitoring system would not generate an alarm during the detection window, the processing unit is arranged to alter the at least one predefined alarm generation criterion by adjusting the specificity of the monitoring system.

In some embodiments the at least one predefined alarm generation criterion comprises a time-based condition. In some such embodiments the processing unit is arranged to alter the at least one predefined alarm generation criterion by altering the time-based condition. In some such embodiments the time-based condition is defined such that a predefined minimum number, N, of consecutive received measured values of the physiological characteristic must meet a predefined abnormality condition in order for the monitoring system to generate an alarm. In some such embodiments the processing unit is arranged to altering the time-based condition by changing the value of N.

In some embodiments the processing unit is arranged to adjust the sensitivity of the monitoring system by:

(i) setting the value of N to a first value, wherein the first value is equal to the greater of: one less than a current value of N and two;

(ii) operating the monitoring system on the basis of the obtained plurality of measured values and the first value of N;

(iii) determining whether operating the monitoring system generated an alarm within the detection window; and (iv) if operating the monitoring system did not generate an alarm within the detection window and the current value of N is greater than two, repeating steps (i)-(iii); or, if operating the monitoring system did not generate an alarm within the detection window and the current value of N is less than or equal to two, setting the value of N to equal two.

In some embodiments the processing unit is arranged to adjust the specificity of the monitoring system by:

(a) setting the value of N to a second value, wherein the second value is one greater than the current value of N;

(b) operating the monitoring system on the basis of the obtained plurality of measured values and the second value of N;

(c) determining whether operating the monitoring system generated an alarm within the detection window; and (d) if operating the monitoring system did not generated an alarm within the detection window, repeating steps (a)-(c).

In some embodiments the processing unit is further arranged to determine whether the obtained plurality of measured values meets at least one predefined quality criterion. In some such embodiments, if the obtained plurality of measured values does not meet the predefined quality criterion, the processing unit is arranged to maintain the current value of the at least one predefined alarm generation criterion.

In some embodiments the processing unit is arranged such that the measurement period begins at least 2 days before the time of the hospitalization.

In some embodiments the processing unit is arranged to obtain data relating to a hospitalization of the subject which comprises information indicating a cause of the hospitalization. In some such embodiments the processing unit is further arranged to determine whether the cause of the hospitalization is related to a health condition being monitored by the monitoring system. In some such embodiments, if the cause of the hospitalization is not related to a health condition being monitored by the system, the processing unit is arranged to maintain the current value of the at least one predefined alarm generation criterion.

In some embodiments the processing unit is in communication with a memory used by the monitoring system to store received measured values, and is arranged to obtain the plurality of measured values by accessing the memory.

In some embodiments the apparatus further comprises a log of alarms without sufficient action. In some such embodiments the processing unit is further arranged to, if the monitoring system would generate an alarm during the detection window based on applying the at least one predefined alarm generation criterion to the obtained plurality of measured values, add an entry to the log of alarms without sufficient action.

Various other embodiments of the apparatus are also contemplated in which the processing unit is further configured to execute any of the above-described method steps.

There is also provided, according to a sixth aspect of the invention, a monitoring apparatus for monitoring a physiological characteristic of a subject. The monitoring apparatus is arranged to receive measured values of a physiological characteristic of a subject and to generate an alarm when the received measured values meet at least one predefined alarm generation criterion. The monitoring apparatus comprises an apparatus for adjusting a monitoring system according to the fourth or fifth aspect.

In some embodiments the monitoring apparatus is for monitoring heart failure, and is arranged to received measured bio-impedance values.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
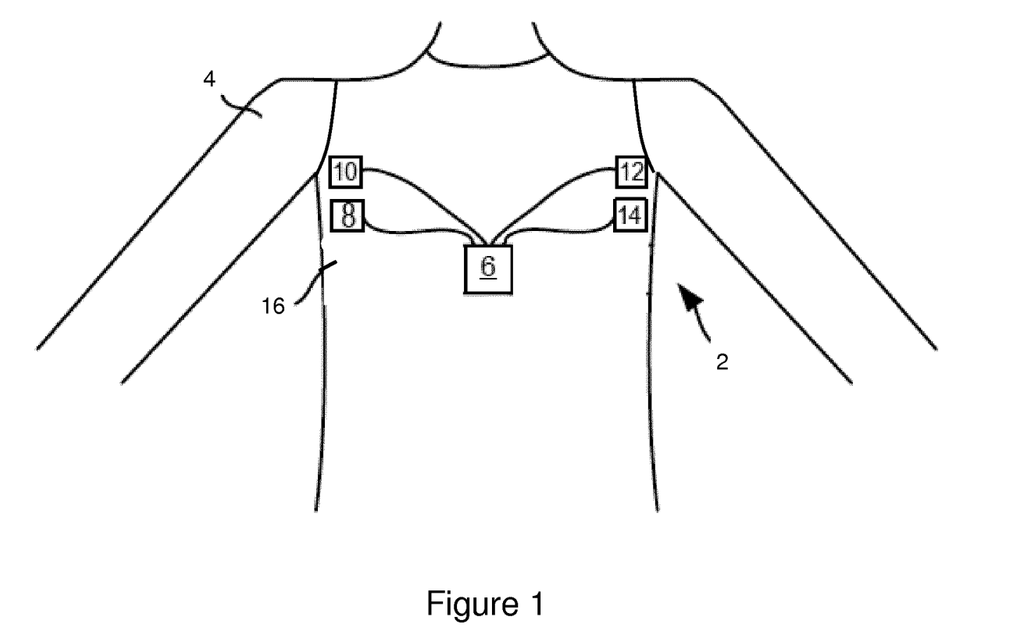
FIG. 1 is an illustration of an apparatus for measuring the fluid content of part of the body of a subject according to an embodiment.

FIG. 1 shows an apparatus for use in monitoring a physiological characteristic of a subject according to the invention. In this particular embodiment, the physiological characteristic is the fluid content of a part of the body of a subject, measured in terms of the resistance of the part of the body of the subject, and thus FIG. 1 shows a measurement device for monitoring fluid content in a part of the body of a subject (patient) using bio-impedance measurements that can implement the method according to the invention. However, those skilled in the art will appreciate that the apparatus can be readily adapted for use in monitoring other physiological parameters through the inclusion or use of a suitable sensor. For example, the apparatus can be used to monitor any of a variety of other physiological characteristics, such as blood pressure, temperature, heart rate, heart rate variability, heart sounds, lung sounds, blood oxygen saturation ($SpO_2$) etc. using sensors suitable for measuring those characteristics.

The measurement device 2 is shown in FIG. 1 as being incorporated in a vest 16, for instance a worn-around vest, worn by a subject 4, although it will be appreciated that other arrangements are possible, such as a shirt, a back-pack, a patch, a strap or belt. In an exemplary embodiment, the patch made of flexible or semi-flexible material, with at least one layer of bio-compatible material such as to affix the patch to the body of the subject 4 is configured to be worn continuously or semi-continuously by the subject 4. In some embodiments the electrodes are embedded into handles, for holding in the subject's hands, into wrist bands worn around the subject's wrists, into rings worn in the subject's fingers, attached to the measurement device. The measurement device 2 comprises a control unit 6 that is connected to electrodes 8, 10, 12, 14 that are to be attached to, or otherwise placed into contact with, the skin of the subject 4. In the illustrated embodiment two pairs of electrodes are provided, although it is possible to use more or fewer electrode pairs. A first pair of electrodes 8, 12 deliver a small electric current at one or more selected frequencies across the chest of the subject 4. A second pair of electrodes 10, 14, each placed near a respective one of the electrodes 8, 12 in the first pair, are placed on the skin of the subject 4 to measure the differential potential across the chest of the subject 4. Where, as in the illustrated embodiment, the measurement device 2 is to monitor the fluid accumulation in the lungs of the subject 4 and is incorporated into a vest 16, the electrodes in each pair are placed on opposite sides of the thorax of the subject 4. The illustrated measurement device 2 is therefore a non-invasive trans-thoracic bio-impedance measurement system.

If the tissue in the body part being measured contains a high level of fluid, it conducts electricity better and thus its impedance is lower than if it contains less fluid. By measuring the impedance at different frequencies the resistance of extracellular fluid ($R_e$) in the tissue can be estimated separately from the resistance of the intracellular fluid ($R_i$) using the Cole-Cole model. In particular, at low measurement frequencies (e.g. approaching 0 Hz) the measured biological tissue impedance is mainly determined by the extracellular fluid content and its characteristics. At these low frequencies, the injected current does not easily pass through cell membranes. At higher frequencies the electrical properties of the biological tissue are determined by both the intracellular and extracellular fluid content as the injected current is able to pass through the cell membranes. Therefore, the influence of the intra- and extra-cellular fluid content on the measured bio-impedance depends on the frequency of the injected current. This allows a characterization of the electrical properties of the biological tissue according to the Cole-Cole model. Using measurements at multiple frequencies allows the approximation by interpolation of the electrical properties of the tissue at direct current (DC, frequency of zero Hz) when the extracellular fluid content is the main component of the impedance.

Where, in alternative or additional embodiments, the measurement device 2 is to be used to monitor the subject for dehydration, the overall resistance of the tissue (i.e. including both the intra-cellular $R_i$ and extra-cellular $R_e$ components) or the intra-cellular resistance $R_i$ can be determined from the measured biological tissue impedance.

The estimation of $R_e$ and/or $R_i$ values from impedance measurements can be performed by a processing unit in the control unit 6. The control unit 6 can also implement the method described below and shown in FIG. 2. Alternatively, the control unit 6 can transmit the impedance measurements or estimated $R_e$ and/or $R_i$ values to another apparatus (such as a smart phone, laptop computer, desktop computer or other processing device) that comprises a processing unit that processes the impedance measurements to produce $R_e$ and/or $R_i$ values (if required) and that implements the other steps in the method shown in FIG. 2.

In alternative implementations, an apparatus that comprises two spatially and electrically separated electrodes for surgical implantation into the tissue of a subject's body can be used to collect the bio-impedance measurements. The person skilled in the art will also be aware of other types of systems to that shown in FIG. 1 that can be used to provide bio-impedance measurements.

Figure 2:
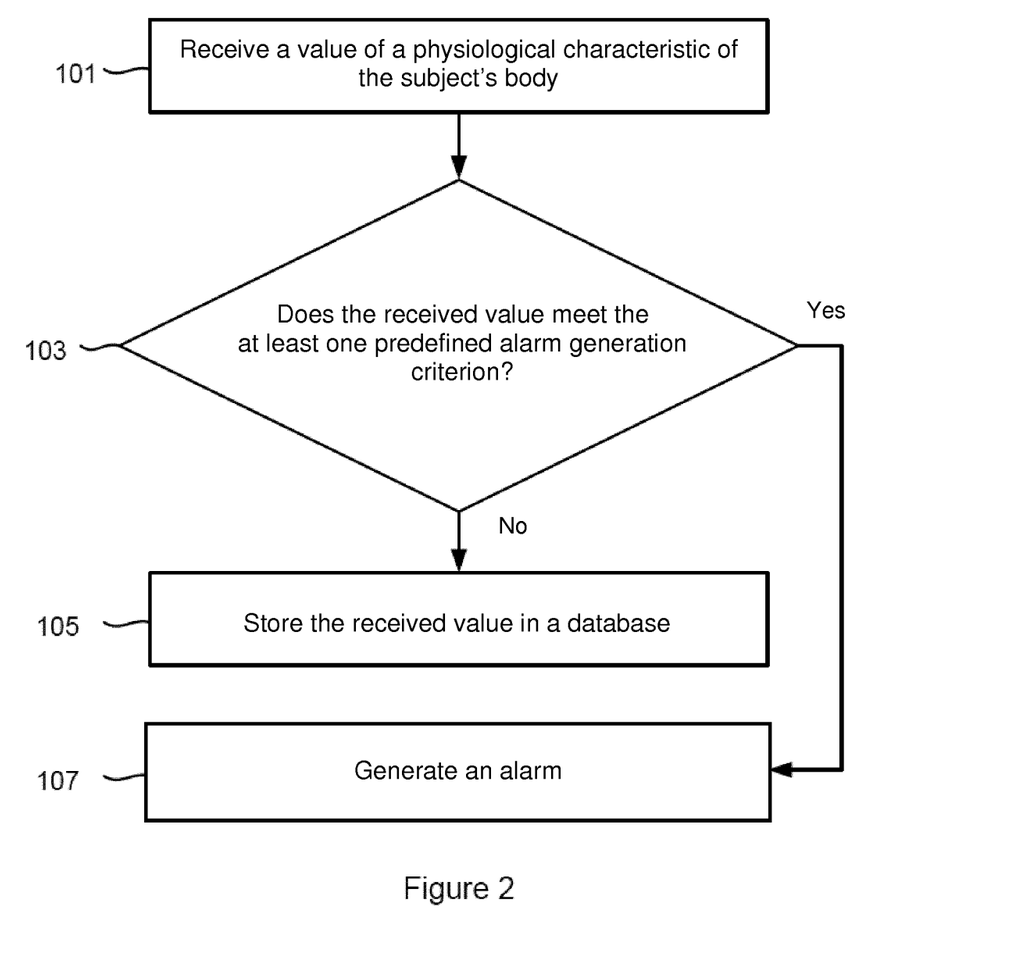
FIG. 2 is a flow chart illustrating a system for monitoring a physiological characteristic of a subject.

FIG. 2 shows a process used by a monitoring system for monitoring a physiological characteristic (e.g. bio-impedance) of a subject. In some embodiments the monitoring system is a software program, e.g. installed on the control unit 6 of the measurement device 2, or on a computer remote from the measurement device 2, to which the measurement device 2 is arranged to send data. In some embodiments the monitoring system is a stand-alone device, having a communications interface for receiving data and a processing unit arranged to perform the process of FIG. 2. The monitoring system is arranged to generate alarms, for example in the format of a text message, a paging message, an e-mail, a sound, a flashing light, or any combination of these or other alarm formats. In some embodiments the monitoring system includes one or more alarm generators (e.g. an e-mail or text messaging program together with an appropriate telecommunications connection). In other embodiments the monitoring system is configured to send a control signal to a remote alarm generator to cause the remote alarm generator to emit an alarm.

In step 101 of the process a new measured value of the physiological characteristic of the body of the subject is received or obtained by the monitoring system, for example from bio-impedance measurement device 2 which measures the impedance of tissue with a small alternating current (AC) flowing between two electrodes. In some embodiments, the value of the physiological characteristic is the value of the resistance of fluid in a part of the subject's body. In preferred embodiments, the value of the resistance of fluid is the resistance $R_e$ of extracellular fluid in the part of the body of the subject, and more preferably, $R_e$ is the resistance of extracellular fluid in the lungs of the subject. However, in alternative embodiments, the value of the physiological characteristic can be a weight measurement, heart rate measurement, blood pressure measurement or temperature measurement, etc. Preferably a new measured value of the physiological characteristic is received at regular intervals. In preferred embodiments where the physiological characteristic is bio-impedance, a new $R_e$ value is received daily.

In step 103, the received measured physiological characteristic value is compared to at least one predefined alarm generation criterion and it is thereby determined whether to generate an alarm. If the received measured value meets the at least one alarm generation criterion it is determined that an alarm is to be generated. In some embodiments the criterion comprises a predefined abnormality condition for determining whether the received value is abnormal. In some embodiments the predefined abnormality condition comprises a range of healthy values of the physiological characteristic, and is defined such that any value falling outside this range is determined to be abnormal. In some embodiments the predefined abnormality condition comprises a maximum threshold such that any value exceeding the maximum threshold is determined to be abnormal. In other embodiments the abnormality condition comprises a minimum threshold such that any value falling below the minimum threshold is determined to be abnormal. It will be appreciated that the above-mentioned abnormality conditions are examples of value-based conditions, because in each case whether or not a given measured value meets the condition depends on the value itself.

The definition of the at least one predefined abnormality condition depends on whether the method is being used to monitor for high values, low values, or both low and high values of the physiological characteristic. For example, some physiological conditions, such as excess fluid accumulation in the lungs, result in lower bio-impedance values due to excess extracellular water in the body of the subject. In this case, where the method is monitoring the bio-impedance of the subject to detect excess fluid accumulation (and also recovery from excess fluid accumulation), the abnormality condition will be directed to generally treat low values as being abnormal. However, other physiological conditions, such as dehydration, result in higher bio-impedance values. Therefore if the method is used to monitor for dehydration, the abnormality condition will be directed to generally treat high bio-impedance values as being abnormal.

In some embodiments the at least one predefined alarm generation criterion comprises a set of conditions, which must all be met by a given measured value in order for an alarm to be generated. In preferred embodiments the set of conditions comprises a time-based condition and a value-based condition. A time-based condition may, for example, specify a minimum amount of time for which the measured values must have consistently met a value-based condition in order for an alarm to be generated. Alternatively, a time-based condition can specify a minimum number of consecutive measured values which must have met a value-based condition in order for an alarm to be generated. Providing a time-based condition can be advantageous because in some embodiments, a number of consecutive abnormal values may need to be received before an accurate determination can be made that a deterioration of the subject's health condition is occurring (and therefore that an alarm needs to be generated). As a consequence of not immediately generating an alarm in response to the receipt of an abnormal measured value, the number of false alarms caused by erroneous measurements (e.g. due to incorrect sensor placement or inconsistent measurement conditions) is reduced.

In a particular preferred embodiment, the at least one predefined alarm generation criterion comprises an abnormality condition and a time-based condition. The time-based condition is defined such that an alarm is generated if the number of consecutive received measured values (including the current received measured value) which meet the abnormality condition is greater than or equal to a predefined threshold N. The value N of the threshold determines how many consecutive abnormal measured values need to be received before the monitoring system generates an alarm. Thus, in this embodiment the performance of step 103 involves determining whether the current received measured value of the physiological characteristic meets the abnormality condition, and if it does, determining how many consecutive measured values received immediately prior to the current received value were also abnormal. In some embodiments this determination is achieved by incrementing a counter each time a received value is determined to be abnormal (and resetting the counter to zero each time a received value is not determined to be abnormal). This number (e.g. the current value of the counter) is then compared to the predefined threshold N.

If the number of consecutive abnormal values (including the current value) is less than N, then the at least one predefined alarm generation criterion is not met. An alarm is not generated, and instead at step 105 the received measured value is simply stored in a memory (e.g. of the control unit 6, or of a remote device with which the control unit 6 is in communication).

If the number of consecutive abnormal values (including the current value) is greater than or equal to N, then the at least one predefined alarm generation criterion is met. In this case an alarm is generated at step 107. In some embodiments the received measured value is also stored in a memory if an alarm is generated. In some embodiments information about the alarm (e.g. the time of generation) is also stored in the memory.

N can take any positive integer value, however the larger the value of N, the longer it will take the monitoring system to detect a deterioration in the subject's health condition (e.g. a potentially significant accumulation of fluid). On the other hand, for smaller values of N, the monitoring system will be more likely to generate false alarms on the basis of minor and short-lived abnormalities that are not clinically significant (for example as a result of incorrect electrode placement or the subject being in the wrong posture). The optimum value of N will depend on how frequently a new value is received and on the particular physiological characteristic and/or health condition being monitored. It will also vary from subject to subject, because deterioration timespan is subject-specific, as discussed above. Embodiments of the invention therefore advantageously enable the value of N to be adjusted to an individual subject.

In some embodiments, the initial value for threshold N may be determined based on the historical behaviour of measured values with the suggested measurement method of the subject. This means that previous measurement values obtained prior to previous hospitalization events is used to determine the most suitable N for a specific subject. The most suitable N can be determined e.g. to be the N that minimises the number of false alarms or maximises the number of hospitalization events that were predicted. Similarly, the measurement values recorded during the subject's inpatient stay can be used to determine an initial value of N. Alternatively or in addition, the measurement values recorded during the subject's inpatient stay can be analysed to determine whether the subject deteriorates and/or recovers slowly or quickly. This can be determined from a slope of the measurement values, and the specificity or sensitivity of the monitoring system can be set accordingly to maximise the performance of the system.

Figure 3:
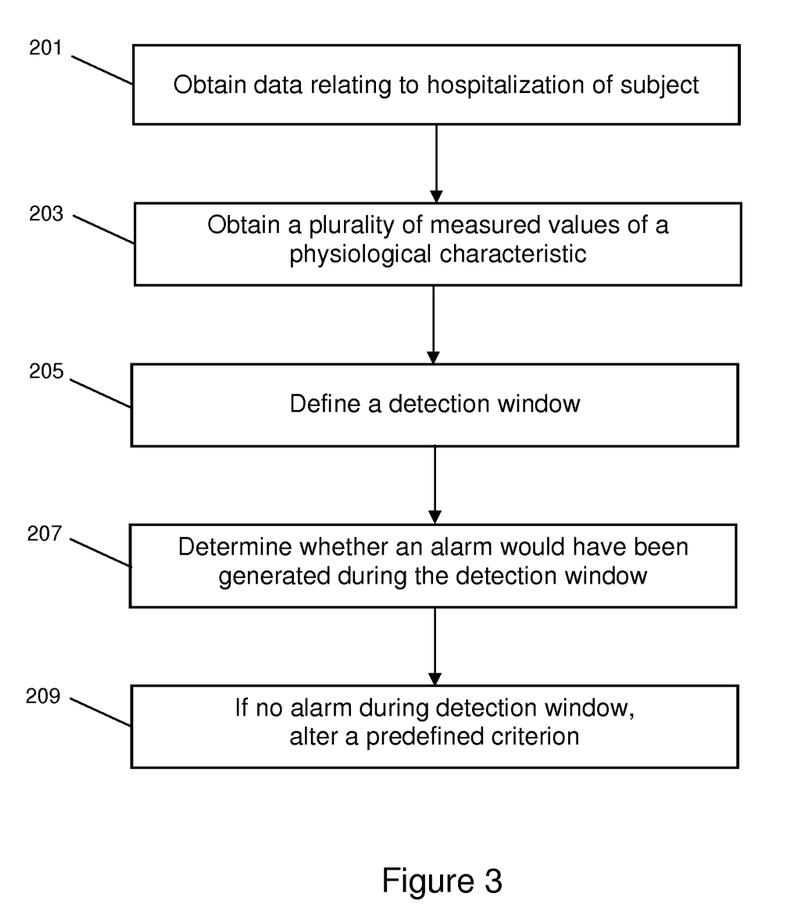
FIG. 3 is a flow chart illustrating a method for adjusting a monitoring system according to a general embodiment of the invention.

FIG. 3 shows a method for adjusting a monitoring system (e.g. a monitoring system which uses the process of FIG. 2) which is arranged to receive measured values of a physiological characteristic of a subject and to generate an alarm when a received measured value meets at least one predefined criterion, according to a general embodiment of the invention. The method bases the adjustment on subject-specific data obtained during a period including a hospitalization of the patient due to deterioration in the health condition being monitored by the monitoring system.

In step 201 data relating to a hospitalization of the subject is obtained. A "hospitalization" is the admittance of a subject to a hospital as an in-patient. It will be appreciated that a particular date and time is associated with any given hospitalization, which is generally recorded by the hospital, e.g. on the subject's medical records and/or on admittance records kept by the hospital. The data relating to a hospitalization of the subject comprises at least a time of the hospitalization. In some embodiments the data also comprises information on the reasons for the hospitalization (e.g. which health condition was involved, the particular symptoms experienced, the acuity of the condition at the time of hospitalization, etc.). In some embodiments the data is obtained directly from a hospital database, e.g. via a communications link between a device being used to perform the method (e.g. the measurement apparatus 2) and a server at the hospital. In other embodiments the data is obtained by a user inputting it into a device being used to perform the method (e.g. manually via a user interface, or via a communications link with a further device).

In step 203 a plurality of measured values of a physiological characteristic are obtained. The plurality of measured values span a measurement period (i.e. the measurement period begins with the earliest measured value in the plurality of measured values and ends with the latest measured value in the plurality of measured values). In preferred embodiments the plurality of measured values comprises a time series of measured values of the physiological characteristic. In some embodiments (i.e. embodiments in which the monitoring system was already being used to monitor the subject during the period leading up to the hospitalization) the pluralilty of measured values are obtained from a memory used by the monitoring system (e.g. a memory of the control unit 6) to store received values.

In alternative embodiments the plurality of measured values may be obtained from a source other than the monitoring system, such as patient records, or a memory associated with a different monitoring system or medical device. It will be appreciated that in such embodiments the monitoring system need not have been already being used to monitor the subject prior to the hospitalization. For example, it in many situations monitoring of a subject with a particular system is started in response to a hospitalization. In such situations, if sufficient data on the physiological characteristic is available from other sources, advantageously the monitoring system can be adjusted to the specific subject immediately, before they even start using it.

In some embodiments the plurality of measured values are obtained directly from a memory accessible by the device being used to perform the method. In alternative embodiments the plurality of measured values are received via a manual user interface of the device or via a communications link with a further device. In some embodiments the plurality of measured values are obtained from a combination of sources (e.g. measured values covering one part of the measurement period are obtained from the monitoring system and measured values covering another part of the measurement period are obtained from a different monitoring system).

The measurement period covers a time period shortly before the time of the hospitalization. In some embodiments the measurement period includes the time of the hospitalization. In alternative embodiments the measurement period ends shortly before the time of the hospitalization. In such embodiments, preferably the measurement period ends not more than 5 days before the time of the hospitalization. In some embodiments the measurement period starts from the time of the earliest available measured value. In other embodiments (e.g. embodiments where measurements are available from a relatively long period (i.e. a month or longer) prior to the hospitalization, the measurement period starts a predetermined length of time (e.g. 20 days) before the time of the hospitalization. In other words, in cases where the subject has been monitored by the monitoring system for a long period of time before the hospitalization (or physiological characteristic data from another source is available covering a long period of time before the hospitalization), only the measured values received during a time period leading up to (and, optionally, immediately following) the hospitalization are used in the adjustment method. In preferred embodiments the measurement period is long enough to encompass the earliest time at which the subject experienced symptoms of the deterioration which led to their hospitalization. In some such embodiments the measurement period covers at least 10 days prior to the time of the hospitalization. In some embodiments the measurement period extends beyond the time of the hospitalization, e.g. if the monitoring system continued to be used whilst the subject was in hospital.

In step 205 a detection window is defined. The detection window is a time period ending at the time of the hospitalization and having a predetermined duration. In preferred embodiments the detection window is defined such that measured values obtained on the day of the hospitalization do not fall within the detection window. The detection window represents the time period during which it is in principle possible to detect the deterioration which led to the hospitalization. The exact duration of the detection window is selectable by a user of the method but should be in the range 3-30 days in order to achieve the beneficial effects of the method. In preferred embodiments the duration of the detection window is in the region of 10-20 days. The length of the detection window is a key input into the adjustment method. If the detection window is too short (i.e. it begins too close to the hospitalization), this can lead to the value of N being increased unnecessarily. If N is too high, alarm generation is delayed beyond the optimal time (i.e. the earliest time at which it can be determined that the subject is experiencing a deterioration in their health condition). If the detection window is too long (i.e. it begins too long before the hospitalization), this can lead to the value of N being left at a low value when it could advantageously be increased. This means that false alarms could occur which would otherwise have been avoided.

In step 207 it is determined whether the monitoring system would generate an alarm during the detection window based on applying the at least one predefined criterion to the obtained plurality of measured values. In some embodiments in which the obtained plurality of measured values comprises measured values received and stored by the monitoring system, the determining comprises checking alarm data stored by the monitoring system to ascertain whether the monitoring system did, in fact, generate an alarm during the detection window (it will be appreciated that if the monitoring system did generate an alarm during the detection window this necessarily implies that an alarm would be generated during the detection window based on applying the at least one predefined criterion to the obtained plurality of measured values). In other embodiments (e.g. embodiments in which the monitoring system was not in use during the measurement period and so the obtained plurality of measured values come from another source) the determining comprises inputting the obtained plurality of measured values to the monitoring system to check whether an alarm is generated in response to any of the measured values (in such cases N will be set to an initial default value, e.g. 2). If an alarm is generated in response to one of the measured values, it is then determined whether the time of that measured value is within the detection window.

If in step 207 it is determined that the monitoring system would generate an alarm during the detection window, then no adjustment is made to the at least one predefined alarm generation criterion. In some embodiments in which the monitoring system was in use during the measurement period and so an alarm was actually generated, an additional step of logging an alarm without sufficient action is performed. In some such embodiments the logging comprises increasing the value of a counter. In some embodiments the logging comprises storing a note that insufficient action (i.e. insufficient to prevent a hospitalization) was taken in response to the alarm. In some embodiments the logging comprises sending an alert, e.g., to a caregiver, that insufficient action was taken in response to an alarm. Advantageously, logging alarms without sufficient action can assist doctors in deciding upon future treatments for the subject because it permits them to easily see which treatments were not successful in the past.

If in step 207 it is determined that the monitoring system would not generate an alarm during the detection window, then in step 209 the at least one predefined alarm generation criterion is altered. In some embodiments determining that that the monitoring system would not generate an alarm during the detection window comprises failing to determine that the system would generate an alarm during the detection window. In some embodiments determining that that the monitoring system would not generate an alarm during the detection window comprises determining that the monitoring system did not generate an alarm during the detection window, e.g. by checking alarm data stored by the system. In some embodiments the altering comprises altering the at least one predefined alarm generation criterion such that the time the monitoring system would generate an alarm when applying the altered predefined alarm generation criterion to the obtained plurality of measured values is within the detection window. In some embodiments altering the at least one predefined alarm generation criterion such that the time the monitoring system would generate an alarm when applying the altered predefined alarm generation criterion to the obtained plurality of measured values is within the detection window comprises altering the at least one predefined alarm generation criterion such that the time at which the monitoring system would generate an alarm based on applying the altered predefined alarm generation criterion to the obtained plurality of measured values is different to the time at which the monitoring system would generate an alarm based on applying the unaltered predefined alarm generation criterion to the obtained plurality of measured values. In some embodiments the altering is performed such that the sensitivity of the monitoring system is adjusted. In some embodiments the altering is performed such that the specificity of the monitoring system is adjusted, alternatively or additionally to the sensitivity of the monitoring system being adjusted. In preferred embodiments, altering the at least one predefined alarm generation criterion comprises altering a time-based condition of the at least one predefined alarm generation criterion. In embodiments in which the time-based condition comprises the threshold N, the altering comprises altering the value of N. In some embodiments the sensitivity of the monitoring system can be adjusted by decreasing N. In some embodiments the specificity of the monitoring system can be adjusted by increasing N.

Figure 4:
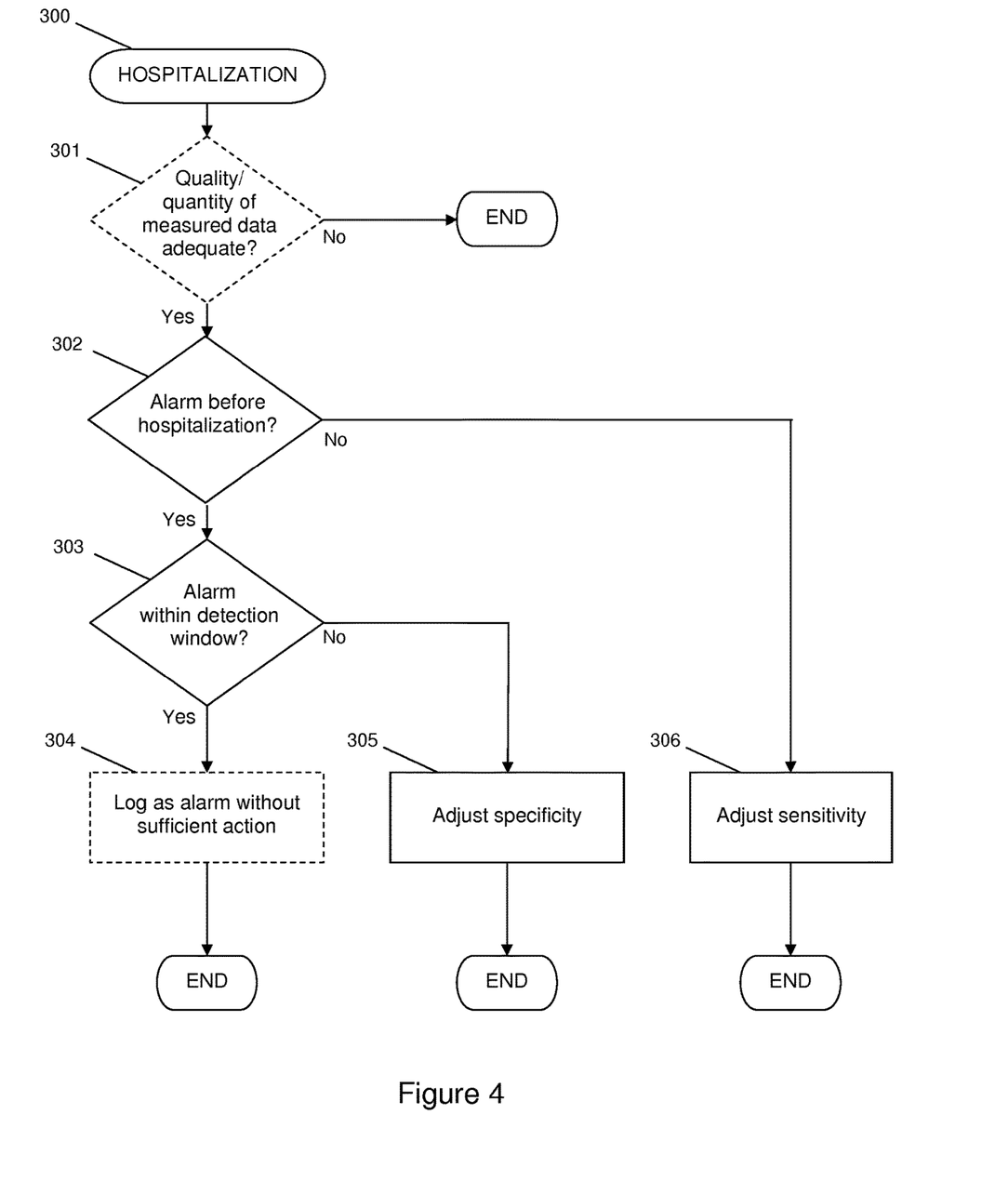
FIG. 4 is a flow chart illustrating a method for adjusting a monitoring system according to a specific embodiment of the invention
Figure 5:
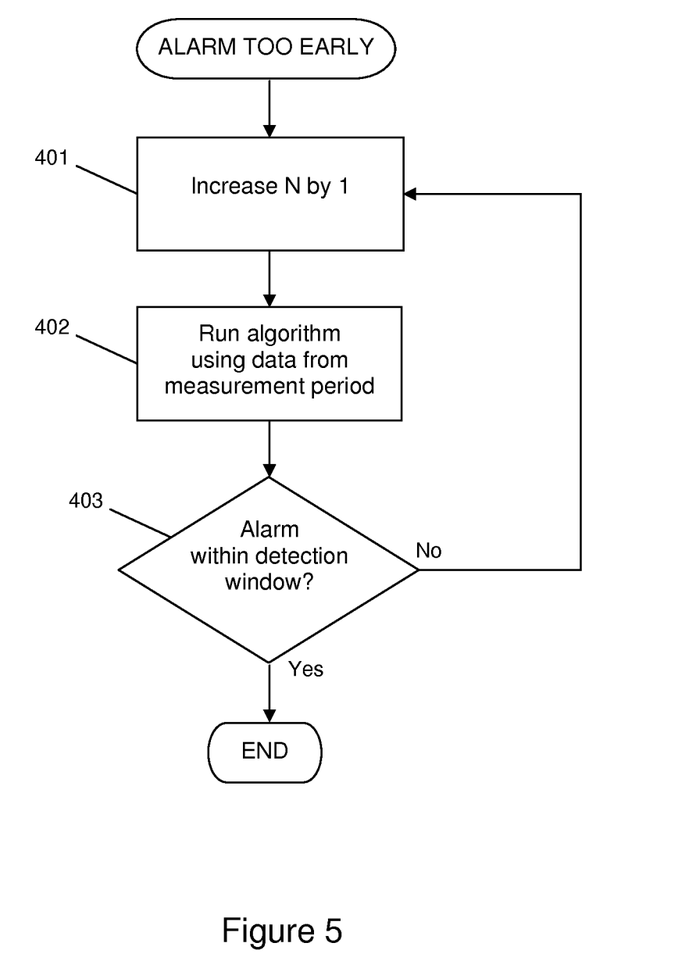
FIG. 5 is a flow chart illustrating a specificity adjustment process used by the method of FIG. 4.
Figure 6:
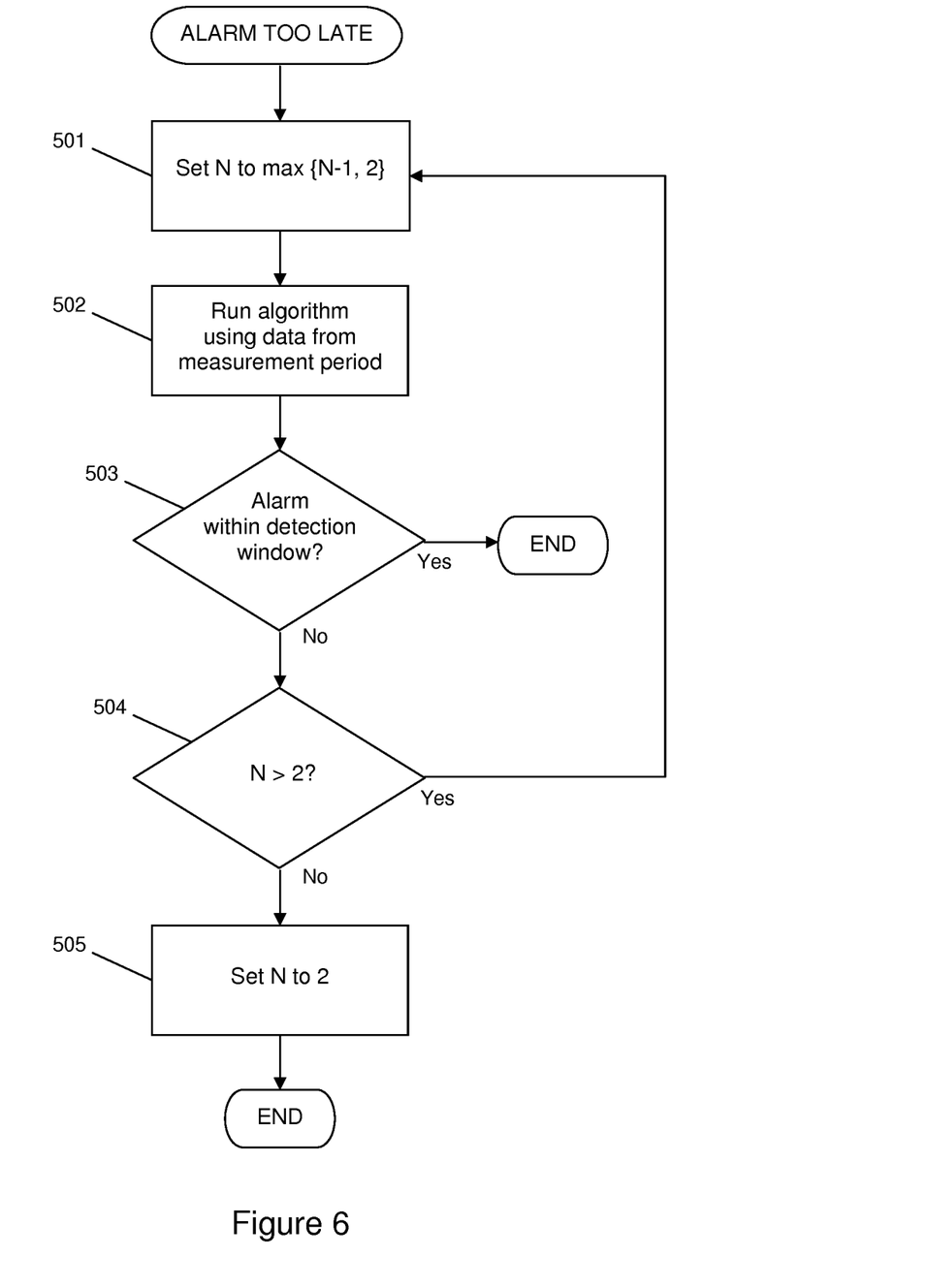
FIG. 6 is a flow chart illustrating a sensitivity adjustment process used by the method of FIG. 4.

FIGS. 4-6 show a specific embodiment of the invention applied to a monitoring system in which the predefined alarm generation criterion comprises an abnormality condition and a time-based condition. The time-based condition is defined such that an alarm is generated if the number of consecutive received measured values (including the current received measured value) which meet the abnormality condition is greater than or equal to a predefined threshold N. The adjustment method shown in FIGS. 4-6 personalizes the value of N to a specific subject based on data relating to a hospitalization of that subject. Steps represented by boxes having dashed lines are optional.

The method is performed in response to a hospitalization 300 of the subject as a result of a deterioration of a health condition of interest (i.e. a health condition for which the subject was being monitored at the time of the hospitalization, such as heart failure). In some embodiments the method additionally includes an initial step of determining whether a given hospitalization of the subject is as a result of a deterioration of a health condition of interest. In such embodiments the method is only performed if it is determined that the hospitalization is a result of a deterioration in a health condition of interest.

As described above, measured values spanning a measurement period including the time of the hospitalization 300 are obtained. In order for the adjustment method to produce beneficial results, it is necessary for the measured values to be sufficiently frequent across the measurement period. Therefore in some embodiments of the invention a check 301 is performed on the quality and/or quantity of the measured values. In some such embodiments the check 301 involves determining whether a minimum frequency of the measured values is met. In some embodiments in which the measured values are obtained daily, the minimum frequency is at least one measured value for every two day period. It will be appreciated, however, that a lower or higher minimum frequency could be used. For example, in some alternative embodiments the minimum frequency is at least three measured values for every seven day period. It will also be appreciated that the beneficial effects produced by the adjustment method may be compromised if a lower minimum frequency is used. In some embodiments the check 301 involves determining how many of the measured values comprise "isolated" abnormal values (i.e. values which meet the abnormality condition, for which the immediately preceding and following measured values do not meet the abnormality criterion). In some such embodiments the check 301 involves determining whether the number of isolated abnormal values is below a predefined threshold. If the result of the check 301 is that the quality and/or quantity of the obtained measured values is insufficient (e.g. because the frequency is too low, and/or the number of isolated abnormal values is too high), then the remaining steps will not be performed. If, on the other hand, the result of the check 301 is that the quality and/or quantity of the obtained measured values is sufficient, the method proceeds to step 205 in which a detection window is defined as described above in relation to FIG. 3.

In the specific embodiment shown in FIG. 4, the determination 302 of whether the monitoring system would generate an alarm within the detection window is performed in two stages. Firstly it is determined 302 whether an alarm would be generated before the hospitalization 300. An alarm generated on the day of the hospitalization or after the hospitalization 300 is determined not to be generated before the hospitalization. If the outcome of the determination 302 is that an alarm would not be generated before the hospitalization, this implies that the alarm would have be generated too late. To correct this, the sensitivity of the monitoring system is adjusted 306. If, on the other hand, the outcome of the determination 302 is that an alarm would be generated before the hospitalization 300, then in a second stage it is determined 303 whether the alarm would be generated within the detection window. If the result of the determination 303 is that an alarm would not be generated within the detection window, this implies that the alarm would be generated too early. To correct this, the specificity of the monitoring system is adjusted 305.

If, on the other hand, the result of the determination 303 is that an alarm would be generated within the detection window, optionally an alarm without sufficient action is logged 304 and the method is complete. It will be appreciated that an alarm without sufficient action is only logged in embodiments where the monitoring system was actually being used to monitor the subject during the measurement period.

The specificity adjustment process used by the method of FIG. 4 is shown in FIG. 5. In step 401 the value of N is increased by 1. Then, in step 402 the monitoring system is operated (i.e. the process of FIG. 2 is performed) using the obtained measured values as the input (and using the new value of N). In step 403 it is determined whether operating the system resulted in the generation of an alarm within the detection window. If no alarm was generated within the detection window, step 401 is repeated so that the value of N is increased by a further increment. Steps 402 and 403 are then performed again using the new value of N. Steps 401-403 are repeated until the outcome of step 403 is that an alarm is generated which is within the detection window. If it is determined in step 403 that an alarm was generated within the detection window, the adjustment method is complete.

Thus the process of FIG. 5 increases the value of N, so that the monitoring system requires more consecutive abnormal values to be received before it generates an alarm. It will be appreciated from FIG. 4 that this process is only performed when it is determined that an alarm would be generated too early to fall within the detection window, meaning that an alarm was being generated before it would in principle have been possible to detect the deterioration which led to the hospitalization. Thus performing the process of FIG. 5 advantageously reduces the false positive rate of the monitoring system, and thus improves its specificity.

FIG. 6 illustrates the sensitivity adjustment process used by the method of FIG. 4. In step 501 of the sensitivity adjustment process N is set to the larger of N−1 and 2 (with N−1 being the value one less than the current value of N). Then, in step 502 the monitoring system is operated using the obtained measured values as the input (and using the new value of N). In step 503 it is determined whether operating the monitoring system resulted in the generation of an alarm within the detection window. If step 503 results in a positive determination, the adjustment method is complete. If the outcome of step 503 is that no alarm was generated within the detection window, then in step 504 it is determined whether the current value of N (i.e. the value that was set in step 501) is greater than 2. If the current value of N is determined to be greater than 2, step 501 is repeated so that the value of N is again set to the greater of n−1 and 2. Steps 502 and 503 are then performed again using the new value of N. Steps 501-503 are repeated until either the outcome of step 503 is that an alarm is generated within the detection window, or the outcome of step 504 is that the current value of N is less than or equal to 2. If it is determined in step 504 that the value of N is less than or equal to 2, then the value of N is set to 2 and the adjustment method is complete. It will be appreciated that the value 2 is used in the sensitivity adjustment process because if N was set smaller than 2, it would lead to false alarms frequently being generated on the basis of isolated abnormal values, e.g. resulting from measurement errors.

Thus the process of FIG. 6 reduces the value of N (whilst ensuring that it cannot be less than 2), so that the monitoring system requires fewer consecutive abnormal values to be received before it generates an alarm. It will be appreciated from FIG. 4 that this process is only performed when it is determined that an alarm would be generated too late, meaning that prevention of the hospitalization 300 would not have been possible. This advantageously reduces the false negative rate of the monitoring system, and thus improves its sensitivity.

There is therefore provided a method and apparatus that allow a subject to be monitored so as to detect and/or predict the onset of or recovery from clinically significant conditions using measurements of one or more physiological characteristics of the subject.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for adjusting a monitoring system, wherein the monitoring system is arranged to receive measured values of a physiological characteristic of a subject and to generate an alarm when the received measured values meet at least one predefined alarm generation criterion; the method comprising:
   obtaining data relating to a hospitalization of the subject, the data comprising a time of the hospitalization, the time of hospitalization comprising an actual time of admittance of the subject to a hospital as an in-patient;
   obtaining a plurality of measured values of the physiological characteristic measured during a measurement period preceding the time of the hospitalization or a measurement period preceding and including the time of the hospitalization;
   defining a detection window as a time period ending with the time of the hospitalization and having a predetermined duration;
   determining whether the monitoring system would generate an alarm during the detection window based on applying the at least one predefined alarm generation criterion to the obtained plurality of measured values; and
   if the monitoring system would not generate an alarm during the detection window, altering the at least one predefined alarm generation criterion such that a time at which the monitoring system would generate an alarm based on applying the altered predefined alarm generation criterion to the obtained plurality of measured values is within the detection window.

2. The method of claim 1, further comprising a step of:
   determining whether the monitoring system would generate an alarm before the time of the hospitalization based on applying the at least one predefined alarm generation criterion to the obtained plurality of measured values;
   wherein if it is determined that the monitoring system would not generate an alarm before the time of the hospitalization, altering the at least one predefined alarm generation criterion comprises adjusting the sensitivity of the monitoring system; and
   wherein if it is determined that the monitoring system would generate an alarm before the time of the hospitalization but not during the detection window, altering the at least one predefined alarm generation criterion comprises adjusting the specificity of the monitoring system.

3. The method of claim 1, wherein the at least one predefined alarm generation criterion comprises a time-based condition, and wherein altering the at least one predefined alarm generation criterion comprises altering the time-based condition.

4. The method of claim 3, wherein the time-based condition is defined such that a predefined minimum number, N, of consecutive received measured values of the physiological characteristic must meet a predefined abnormality condition in order for the monitoring system to generate an alarm, and wherein altering the time-based condition comprises changing the value of N.

5. The method of claim 4, wherein adjusting the sensitivity of the monitoring system comprises:
   setting the value of N to a first value, wherein the first value is equal to the greater of: one less than a current value of N and two;
   operating the monitoring system on the basis of the obtained plurality of measured values and the first value of N;

determining whether operating the monitoring system generated an alarm within the detection window; and if operating the monitoring system did not generate an alarm within the detection window and the current value of N is greater than two, repeating the setting, the operating, and the determining whether operating the monitoring system generated the alarm within the detection window; or, if operating the monitoring system did not generate an alarm within the detection window and the current value of N is less than or equal to two, setting the value of N to equal two.

6. The method of claim 4, wherein adjusting the specificity of the monitoring system comprises:

setting the value of N to a second value, wherein the second value is one greater than the current value of N;

operating the monitoring system on the basis of the obtained plurality of measured values and the second value of N;

determining whether operating the monitoring system generated an alarm within the detection window; and if operating the monitoring system did not generated an alarm within the detection window, repeating the setting of the value of N to a second value, the operating of the monitoring system on the basis of the obtained plurality of the measured values and the second value of N, and the determining whether the operating the monitoring system generated the alarm within the detection window.

7. The method of claim 1, further comprising:

determining whether the obtained plurality of measured values meets at least one predefined quality criterion; and if the obtained plurality of measured values does not meet the predefined quality criterion, maintaining the current value of the at least one predefined alarm generation criterion.

8. The method of claim 1, wherein the measurement period begins at least two days before the time of the hospitalization.

9. The method of claim 1, wherein the data relating to a hospitalization of the subject comprises information indicating a cause of the hospitalization, and wherein the method further comprises:

determining whether the cause of the hospitalization is related to a health condition being monitored by the monitoring system; and if the cause of the hospitalization is not related to a health condition being monitored by the system, maintaining the current value of the at least one predefined alarm generation criterion.

10. A computer program product, comprising computer readable code embodied therein, the computer readable code being configured such that, on execution by a suitable computer or processor, wherein the computer or processor is arranged to receive measured values of a physiological characteristics of a subject, the computer or processor:

obtains data relating to a hospitalization of the subject, the data comprising a time of the hospitalization, the time of hospitalization comprising an actual time of admittance of the subject to a hospital as an in-patient;

obtains a plurality of measured values of the physiological characteristic measured during a measurement period preceding the time of the hospitalization or a measurement period preceding and including the time of the hospitalization;

defines a detection window as a time period ending with the time of the hospitalization and having a predetermined duration;

determines whether the monitoring system would generate an alarm during the detection window based on applying the at least one predefined alarm generation criterion to the obtained plurality of measured values; and if the monitoring system would not generate an alarm during the detection window, alters the at least one predefined alarm generation criterion such that a time at which the monitoring system would generate an alarm based on applying the altered predefined alarm generation criterion to the obtained plurality of measured values is within the detection window.

11. An apparatus for adjusting a monitoring system, wherein the monitoring system is arranged to receive measured values of a physiological characteristic of a subject and to generate an alarm when the received measured values meet at least one predefined alarm generation criterion, the apparatus comprising:

a processing unit arranged to:

obtain data relating to a hospitalization of the subject, the data comprising a time of the hospitalization, the time of hospitalization comprising an actual time of admittance of the subject to a hospital as an in-patient;

obtain a plurality of measured values of the physiological characteristic measured during a measurement period preceding, and optionally including, the time of the hospitalization;

define a detection window as a time period ending with the time of the hospitalization and having a predetermined duration;

determine whether the monitoring system would generate an alarm during the detection window based on applying the at least one predefined alarm generation criterion to the obtained plurality of measured values; and if the monitoring system would not generate an alarm during the detection window, alter the at least one predefined alarm generation criterion such that a time at which the monitoring system would generate an alarm based on applying the altered predefined alarm generation criterion to the obtained plurality of measured values is within the detection window.

12. The apparatus of claim 11, wherein the processing unit is in communication with a memory used by the monitoring system to store received measured values, and is arranged to obtain the plurality of measured values by accessing the memory.

13. The apparatus of claim 12, wherein the apparatus further comprises a log of alarms without sufficient action, and wherein the processing unit is further arranged to:

if the monitoring system would generate an alarm during the detection window based on applying the at least one predefined alarm generation criterion to the obtained plurality of measured values, add an entry to the log of alarms without sufficient action.

14. The apparatus of claim 11, wherein the apparatus comprises a monitoring apparatus.

15. The apparatus of claim 14, wherein the processing unit is arranged to monitor for heart failure, and is arranged to receive measured bio-impedance values.

* * * * *